United States Patent [19]

Dickson

[11] Patent Number: Plant 7,312

[45] Date of Patent: Sep. 4, 1990

[54] ROSE PLANT DICMADDER

[75] Inventor: Patrick Dickson, Newtownards, Northern Ireland

[73] Assignee: Jackson & Perkins Company, Medford, Oreg.

[21] Appl. No.: 319,649

[22] Filed: Mar. 6, 1989

[51] Int. Cl.[5] ..... A01H 5/00

[52] U.S. Cl. ..... Plt./1

[58] Field of Search ..... Plt. 1, 4, 7, 17, 10.1, Plt./16

*Primary Examiner*—Howard J. Locker

*Attorney, Agent, or Firm*—Majestic, Parsons, Siebert & Hsue

[57] ABSTRACT

A rose variety of the Shrub class is provided having bright orange with light reverse flowers, upright, well branched growth habit, glossy green, disease resistant foliage and vigor and hardiness.

1 Drawing Sheet

SUMMARY OF THE DISCOVERY

The present discovery relates to a new and distinct variety of rose plant of the Shrub class. The new variety is the result of crossing an unnamed breeding line of the inventor by another unnamed breeding line of the inventor. The female breeding line is a low growing (about 2½ feet) pink shrub or patio rose (the latter being the commercial definition given to shrub-like, low growing varieties with continuous bloom in England) that has small, green and glossy foliage. The leaves average about 2 inches in length, the flower is simple with 5 petals and is about 1½ to 2 inches in diameter when fully open. The male parent is a large shrub to 5 feet in height with simple orange and yellow flowers average 3 inches in diameter. The male parent flowers heavily only in the first spring flush of bloom. Its foliage is dull, matte green and fairly large (about 4½ to 5 inches long).

The primary objective of this breeding was to produce a new rose variety of the Shrub class which produces a profusion of bright flowers on a compact, healthy plant. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Bright orange with light reverse flowers.
2. Upright, well branched growth habit.
3. Glossy green, disease resistant foliage.
4. Vigor and hardiness.

The new variety has the flower color of the male parent, but has the continuous blooming characteristic of the female parent. The foliage is similar to the female parent in color and size.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE DISCOVERY

The following is a detailed description of my new rose cultivar, which has been denominated "Dicmadder". Color terminology is in accordance with The Royal Horticultural Society Colour Chart except where an ordinary dictionary significance for the color is apparent.

Observations of the buds and flowers were made from specimens grown in a garden environment at Somis, Calif. from September to November.

Flower

The blooming habit is continuous. The bud size is one half inch when the petals start to unfurl. The bud form is short and of a pointed ovoid shape. The bud color when sepals first divide is near Orange Red Group 32B to 32C; when half blown the upper side of the petals is near Orange Red Group 32A, and the lower side of petals ranges from near White Group 155B at the point of attachment, to Orange Red Group 32B to 32D at the edge of the petal. The sepals have a color near Green Group 138C. The surface texture is covered in fine hairs. There are three normally appendage sepals, and two unappendaged sepals with hairy edge. The receptacle color is near Green Group 138A, funnel shaped, and small in size, with a hairy, glandular surface. The peduncle is of short length and glandular surface. Peduncle color is medium green, and the peduncle is stiff and erect.

Bloom

Bloom size is small, with an average open size of one and one half inches, borne several together in clusters.

The clusters are rounded. The stems are strong, and short in length. Flowers are usually presented one to five per flowering stem. The form when first opened is flat and retained to the end with outer petal edges slightly curved. Under normal conditions there are five petals. The upper side of petals at the flower center is near Orange Red Group 32A, and the reverse side of the petals ranges from near Orange Red Group 32B to 32D, from the petal edge toward the point of attachment. The base of petals has a small white half moon at the point of attachment. The major color on the upper side is near Orange Red Group 32A. By the end of the third day, there is some fading in bright sun before the petals drop.

There is no fragrance. The petal texture is thick, of a deltoid shape, and the tips are flat and slightly recurved.

The arrangement is imbricated with few petaloids in the center. The blooms drop off cleanly, and last both on the plant and as a cut flower for a fair amount of time.

Reproductive Parts

There are many athers, of yellow color and arranged regularly around the styles. The filaments are yellow, the pollen is lemon yellow, the styles are white and the stigmas are greenish white. Hips normally do not form on the plant, but when they do they are small (generally 1 to 1.5 cm in diameter) and turn bright orange when ripe.

Plant

A vigorous, upright, branching growth of shrub form. The variety is winter hardy to about 20° F. and to lower temperatures if adequate protection is given to protect the plant from wind and temperature extremes. The plant height is about 3 feet under normal growing conditions and about 3 feet wide.

Foliage

Foliage is small in size and of normal quantity. The new foliage is reddish colored. The old foliage is bright glossy green. Normal mid-stem leaves have five to seven leaflets.

The leaflets are of a pointed oval shape and have a glossy texture with a smooth edge. Any serration is single and small. Petiole rachis is green and petiole underside is mostly smooth, with occasional prickles. Stipules are medium and bearded. The foliage is resistant to mildew and blackspot under normal growing conditions at Somis, Calif.

Wood

New wood is light green, with a smooth bark. Old wood is green with a smooth bark.

Prickles

There are an ordinary number of prickles on main cains from the base and on laterals from the main canes. The form is medium and straight. There are few prickles on the main stalks or laterals, as these only occur on peduncles. Color when young is green and remains so.

Parentage

The seed parent was an unnamed seedling. The pollen parent was also an unnamed seedling.

Classification

Botanical is Shrub. Commercial is Shrub.

I claim:

1. A new and distinct variety of rose plant of the Shrub class substantially as herein shown and described, characterized particularly as to novelty by vigorous, hardy plant growth, disease resistant, dark green glossy foliage, upright, well branched habit of growth, and abundant bright orange flowers.

* * * * *

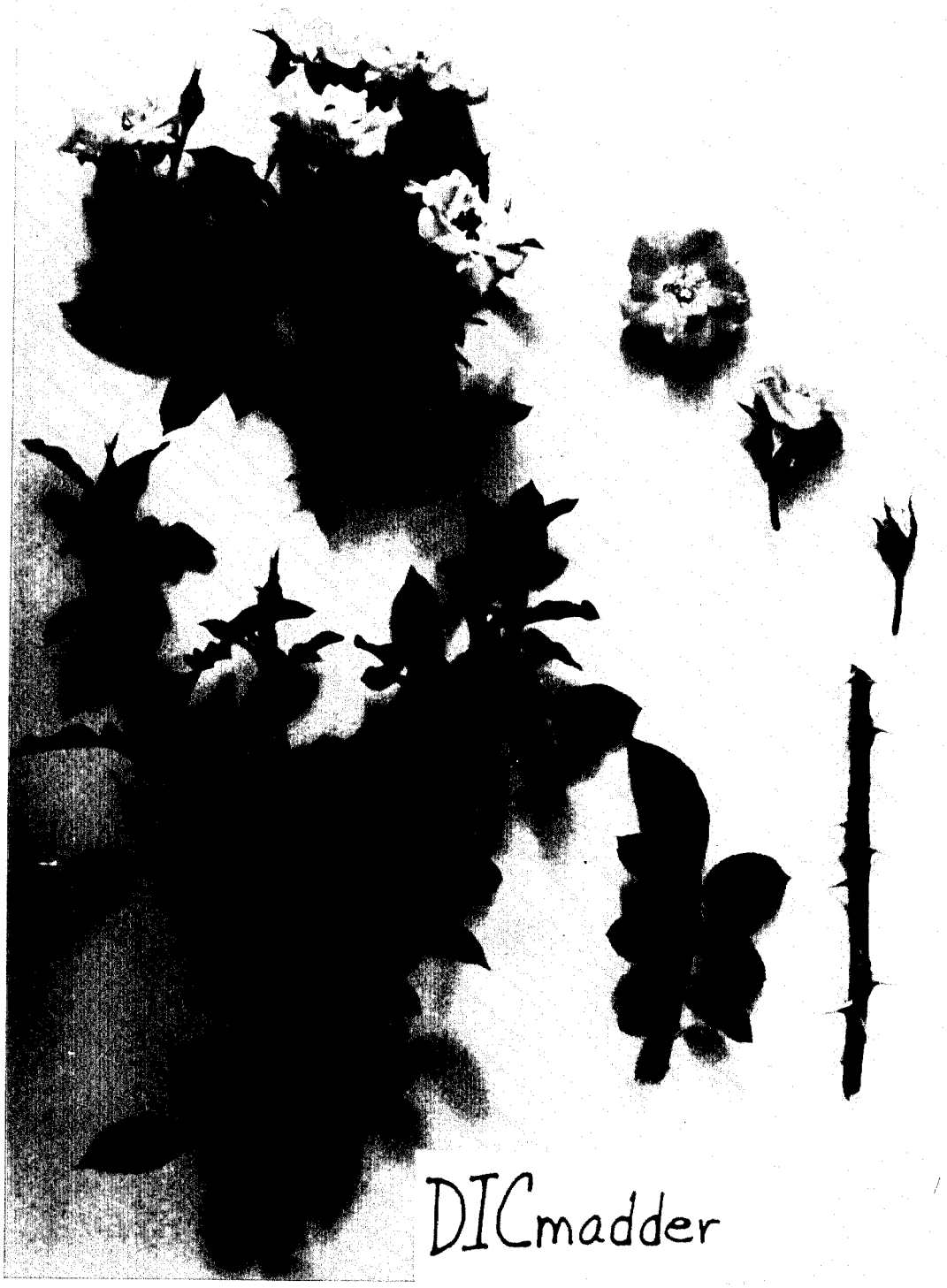
DICmadder